US008649845B2

(12) United States Patent
McIntyre et al.

(10) Patent No.: US 8,649,845 B2
(45) Date of Patent: Feb. 11, 2014

(54) METHODS FOR IDENTIFYING TARGET STIMULATION REGIONS ASSOCIATED WITH THERAPEUTIC AND NON-THERAPEUTIC CLINICAL OUTCOMES FOR NEURAL STIMULATION

(75) Inventors: Cameron C. McIntyre, Cleveland, OH (US); J. Luis Lujan, Mayfield Heights, OH (US); Ashutosh Chaturvedi, Powell, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 46 days.

(21) Appl. No.: 13/317,459

(22) Filed: Oct. 19, 2011

(65) Prior Publication Data
US 2012/0116211 A1 May 10, 2012

Related U.S. Application Data

(60) Provisional application No. 61/394,609, filed on Oct. 19, 2010.

(51) Int. Cl.
*A61B 5/05* (2006.01)
(52) U.S. Cl.
USPC ............ 600/407; 600/409; 600/544; 600/547
(58) Field of Classification Search
USPC ................. 600/407–480, 373–378, 544–549; 607/45–46, 89–131
See application file for complete search history.

(56) References Cited

U.S. PATENT DOCUMENTS

| | | | | |
|---|---|---|---|---|
| 6,246,912 B1 * | 6/2001 | Sluijter et al. | ................ | 607/100 |
| 6,778,846 B1 * | 8/2004 | Martinez et al. | ............. | 600/407 |
| 7,299,096 B2 * | 11/2007 | Balzer et al. | .................... | 607/45 |
| 7,346,382 B2 * | 3/2008 | McIntyre et al. | ............ | 600/407 |
| 7,565,199 B2 * | 7/2009 | Sheffield et al. | ............... | 607/45 |
| 7,680,526 B2 * | 3/2010 | McIntyre et al. | ............ | 600/416 |
| 7,860,548 B2 * | 12/2010 | McIntyre et al. | ............ | 600/407 |
| 7,904,134 B2 * | 3/2011 | McIntyre et al. | ............ | 600/407 |
| 8,180,601 B2 * | 5/2012 | Butson et al. | ..................... | 703/2 |
| 8,195,300 B2 * | 6/2012 | Gliner et al. | .................... | 607/45 |
| 8,257,684 B2 * | 9/2012 | Covalin et al. | .............. | 424/1.89 |
| 8,262,714 B2 * | 9/2012 | Hulvershorn et al. | .......... | 607/88 |
| 2002/0099295 A1 * | 7/2002 | Gil et al. | ...................... | 600/476 |
| 2006/0017749 A1 * | 1/2006 | McIntyre et al. | ............ | 345/664 |
| 2007/0067003 A1 * | 3/2007 | Sanchez et al. | ................ | 607/45 |
| 2007/0083104 A1 | 4/2007 | Butson et al. | | |
| 2008/0039895 A1 * | 2/2008 | Fowler et al. | ..................... | 607/2 |
| 2008/0114233 A1 * | 5/2008 | McIntyre et al. | ............ | 600/407 |

(Continued)

OTHER PUBLICATIONS

USPTO, International Search Report and the Written Opinion of the International Searching Authority, or the Declaration, mailed Dec. 27, 2011 from related International Application No. PCT/US2011/056898.

(Continued)

*Primary Examiner* — Sanjay Cattungal
(74) *Attorney, Agent, or Firm* — Kenyon & Kenyon LLP

(57) ABSTRACT

A method for identifying and activating specific axonal pathways for achieving therapeutic benefits during a neural stimulation, such as deep brain stimulation. Clinical data, diffusion tensor tractography, and computer models of patient-specific neurostimulation may be used to identify particular axonal pathways activated by deep brain stimulation and to determine their correlations with specific clinical outcomes.

34 Claims, 8 Drawing Sheets
(8 of 8 Drawing Sheet(s) Filed in Color)

(56) References Cited

U.S. PATENT DOCUMENTS

| | | | |
|---|---|---|---|
| 2008/0114579 A1* | 5/2008 | McIntyre et al. | 703/11 |
| 2008/0154341 A1* | 6/2008 | McIntyre et al. | 607/59 |
| 2008/0227139 A1* | 9/2008 | Deisseroth et al. | 435/29 |
| 2009/0208073 A1* | 8/2009 | McIntyre et al. | 382/128 |
| 2009/0210208 A1* | 8/2009 | McIntyre et al. | 703/11 |
| 2010/0113959 A1* | 5/2010 | Pascual-Leone et al. | 600/544 |
| 2010/0152604 A1* | 6/2010 | Kaula et al. | 600/546 |
| 2010/0331883 A1* | 12/2010 | Schmitz et al. | 606/249 |
| 2011/0184487 A1* | 7/2011 | Alberts et al. | 607/45 |
| 2011/0196253 A1* | 8/2011 | McIntyre et al. | 600/547 |
| 2011/0213440 A1* | 9/2011 | Fowler et al. | 607/45 |
| 2011/0306845 A1* | 12/2011 | Osorio | 600/300 |
| 2011/0306846 A1* | 12/2011 | Osorio | 600/301 |
| 2012/0089205 A1* | 4/2012 | Boyden et al. | 607/88 |
| 2012/0226138 A1* | 9/2012 | DeSalles et al. | 600/411 |
| 2012/0265262 A1* | 10/2012 | Osorio | 607/3 |

OTHER PUBLICATIONS

An, et al., "Prefrontal cortical projections to longitudinal columns in the midbrain periaqueductal gray in macaque monkeys," J Comp Neurol 401 (4) (1998), pp. 455-479.

Butson, C. R., et al., "Tissue and electrode capacitance reduce neural activation volumes during deep brain stimulation," Clinical Neurophysiology, vol. 116 (2005), pp. 2490-2500.

Butson, C. R., "Patient specific analysis of the volume of tissue activated during deep brain stimulation," NeuroImage, Academic Press, vol. 34, No. 2 (Dec. 2, 2006), pp. 661-670.

Carmichael, S. T., et al., "Connectional networks within the orbital and medial prefrontal cortex of macaque monkeys," J Comp Neurol 371 (2) (1996), pp. 179-207.

Chaturvedi, et al., "Patient-specific models of deep brain stimulation: Influence of field model complexity on neural activation predictions," Brain Stimulation (2010), pp. 65-67.

Croxson, et al., "Quantitative investigation of connections of the prefrontal cortex in the human and macaque using probabilistic diffusion tractography," J Neurosci 25 (39) (2005), pp. 8854-8866.

Frankemolle, et al., "Reversing cognitive-motor impairments in Parkinson's disease patients using a computational modelling approach to deep brain stimulation programming," Brain 133 (2010), pp. 746-761.

Freedman, et al., "Subcortical projections of area 25 (subgenual cortex) of the macaque monkey," J Comp Neurol 421(2) (2000), pp. 172-188.

Giacobbe, et al., "Treatment resistant depression as a failure of brain homeostatic mechanisms: implications for deep brain stimulation," Exp Neurol 219 (1) (2009), pp. 44-52.

Goodman, et al., "Deep brain stimulation for intractable obsessive compulsive disorder: pilot study using a blinded, staggered-onset design," Biol Psychiatry 67 (6) (2010), pp. 535-542.

Greenberg, et al., "Deep brain stimulation of the ventral internal capsule/ventral striatum for obsessive-compulsive disorder: worldwide experience," Mol Psychiatry 15 (1) (2010), pp. 64-79.

Greenberg, et al., "Three-year outcomes in deep brain stimulation for highly resistant obsessive-compulsive disorder," Neuropsychopharmacology 31 (11) (2006), pp. 2384-2393.

Gutman, et al., "A tractography analysis of two deep brain stimulation white matter targets for depression," Biol Psychiatry 65 (4) (2009), pp. 276-282.

Haber, et al., "Reward-related cortical inputs define a large striatal region in primates that interface with associative cortical connections, providing a substrate for incentive-based learning," J Neurosci 26 (32) (2006), pp. 8368-8376.

Haber, et al., "Cognitive and limbic circuits that are affected by deep brain stimulation," Front Biosci 14 (2009), pp. 1823-1834.

Hines, M. L., et al., "The NEURON simulation environment," Neural Comput., 9(6) (Aug. 15, 1997), pp. 1179-1209.

Hua, et al., "Tract probability maps in stereotaxic spaces: analyses of white matter anatomy and tract-specific quantification," Neuroimage 39 (1) (2008), pp. 336-347.

Johansen-Berg, et al., "Anatomical connectivity of the subgenual cingulate region targeted with deep brain stimulation for treatment-resistant depression," Cereb Cortex 18 (6) (2008), pp. 1374-1383.

Kopell, et al., "Deep brain stimulation for psychiatric disorders," J Clin Neurophysiol 2I (1) (2004), pp. 51-67.

Lozano, et al., "Subcallosal cingulate gyrus deep brain stimulation for treatment-resistant depression," Biol Psychiatry 64 (6) (2008), pp. 461-467.

Lujan, et al., "Tracking the mechanisms of deep brain stimulation for neuropsychiatric disorders," Front Biosci 13 (2008), pp. 5892-5904.

Lujan, J.L. et al., "Automated 3-Dimensional Brain Atlas Fitting to Microelectrode Recordings from Deep Brain Stimulation Surgeries," Stereotact. Funct. Neurosurg. 87(2009), pp. 229-240.

Machado, et al., "Functional topography of the ventral striatum and anterior limb of the internal capsule determined by electrical stimulation of awake patients," Clin Neurophysiol 120 (11) (2009), pp. 1941-1948.

Malone, et al., "Deep brain stimulation of the ventral capsule/ventral striatum for treatment-resistant depression," Biol Psychiatry 65 (4) (2009), pp. 267-275.

Mayberg, H. S., et al., "Deep brain stimulation for treatment-resistant depression," Neuron, 45(5) (Mar. 3, 2005), pp. 651-660.

Mayberg, H. S., et al., "Limbic-cortical dysregulation: a proposed model of depression," J Neuropsychiatry Clin Neurosci. 9 (3) (1997), pp. 471-481.

McIntyre, C. C., et al., "Network perspectives on the mechanisms of deep brain stimulation," Neurobiol Dis 38 (3) (2010), pp. 329-337.

McIntyre, C. C., et al., "Modeling the excitability of mammalian nerve fibers: influence of afterpotentials on the recovery cycle," J Neurophysiol, 87(2) (Feb. 2002), pp. 995-1006.

McNeal, et al., "Analysis of a model for excitation of myelinated nerve," IEEE Trans Biomed Eng. 23 (4) (1976), pp. 329-337.

Miocinovic, S., et al., "Cicerone: Stereotactic Neurophysiological Recording and Deep Brain Stimulation Electrode Placement Software System," Acta Neurochirurgica Suppl., vol. 97, No. 2 (Jan. 1, 2007), pp. 561-567.

Miocinovic, S., et al., "Experimental and theoretical characterization of the voltage distribution generated by deep brain stimulation," Exp Neurol 216 (i) (2009), pp. 166-176.

Nuttin, et al., "Electrical stimulation in anterior limbs of internal capsules in patients with obsessive-compulsive disorder," Lancet 354 (9189) (1999), p. 1526.

Saxena, et al., "Cerebral glucose metabolism in obsessive-compulsive hoarding," Am J Psychiatry. 161 (6) (2004), pp. 1038-1048.

Tuch, D S., et al., "Conductivity tensor mapping of the human brain using diffusion tensor MRI," Proc Natl Acad Sci USA, 98(20) (Sep. 25, 2001), pp. 11697-11701.

Viola, et al., "Importance-driven focus of attention," IEEE Trans Vis Comput Graph 12 (5) (2006), pp. 933-940.

Wakana, S., et al., "Reproducibility of quantitative tractography methods applied to cerebral white matter," Neuroimage 36 (3) (2007), pp. 630-644.

Wakana, S., et al., "Fiber tract-based atlas of human white matter anatomy," Radiology, 230 (1) (Jan. 2004), pp. 77-87.

Ward, H. E., et al., "Update on deep brain stimulation for neuropsychiatric disorders," Neurobiol Dis 38 (3) (2010), pp. 346-353.

Zhang, Y., et al., "Atlas-guided tract reconstruction for automated and comprehensive examination of the white matter anatomy," Neuroimage 52(4) (2010), pp. 1289-1301.

\* cited by examiner

| Disorders | Outcome measures | Group | Patient | Score | Improvement (%) | Active axon fiber number 1 2 3 4 5 6 7 ... 2285/60 |
|---|---|---|---|---|---|---|
| TRD | HD#5 | Remission (1.1) | CC1 | 9 | 73 | x x x x x / x x / x x x x / x x x x x |
| | | | CC4 | 1 | 97 | |
| | | | CC6 | 1 | 97 | |
| | | | CC7 | 2 | 92 | |
| | | | CC8 | 0 | 100 | |
| | | Non-remission clinical response (1.2) | n/a | n/a | n/a | |
| | | No response (1.3) | CC2 | 27 | 0 | x / [x] [x] / x |
| | | | CC3 | 34 | 8 | [x] [x] / [x] |

Fig. 6

METHODS FOR IDENTIFYING TARGET STIMULATION REGIONS ASSOCIATED WITH THERAPEUTIC AND NON-THERAPEUTIC CLINICAL OUTCOMES FOR NEURAL STIMULATION

CROSS-REFERENCE TO RELATED APPLICATION

The present application claims priority to U.S. Provisional Patent Application No. 61/394,609, filed Oct. 19, 2010, the entire contents of which is hereby incorporated by reference herein.

GOVERNMENT RIGHTS

Using the specific language required by 37 C.F.R. §401.14 (f)(4): This invention was made with government support under grant number R01 NS059736 awarded by the National Institutes of Health (NIH). The government has certain rights in the invention.

FIELD OF THE INVENTION

The present invention relates to methods for treating psychiatric disorders and other disorders by identifying and activating stimulation target regions to achieve therapeutic benefits.

BACKGROUND

Deep brain stimulation (DBS) for psychiatric disorders represents a promising new application of an established medical technology. DBS trials for treatment of psychiatric disorders have demonstrated significant therapeutic benefit. However, precise therapeutic mechanisms, optimal target stimulation sites or regions, and specific axonal pathways responsible for therapeutic benefits have yet to be explicitly defined.

A significant number of psychiatric patients, such as patients diagnosed with treatment-resistant depression (TRD) or obsessive compulsive disorder (OCD) who have undergone multiple pharmacological and behavioral treatments, still remain severely disabled. For these patients, deep brain stimulation (DBS) represents a surgical alternative that has demonstrated encouraging therapeutic results in early stage clinical trials (Lozano, A. M. et al., "Subcallosal cingulate gyrus deep brain stimulation for treatment-resistant depression," Biol. Psychiatry 64 (6), 461-467 (2008) (hereinafter "Lozano et al., 2008"), the entire contents of which is hereby incorporated by reference herein). However, anatomical target sites or regions to be stimulated and stimulation settings for optimal clinical outcomes remain unclear.

Recent scientific efforts have focused on defining the organization and structural connectivity of neural networks associated with psychiatric disease. Prevailing hypotheses suggest that these therapeutic benefits are brought forth by stimulation-dependent regulation of abnormal network activity (McIntyre, C. C. et al., "Network perspectives on the mechanisms of deep brain stimulation," Neurobiol. Dis. 38 (3), 329-337 (2010) (hereinafter "McIntyre et al., 2010"), the entire contents of which is hereby incorporated by reference herein). Unfortunately, definition of precise therapeutic mechanisms and optimal target stimulation sites or regions remains restricted by limited characterization of the specific neuronal effects of DBS.

Converging biochemical and functional imaging studies have provided insight into complex cortico-striato-thalamo-cortical (CSTC) networks associated with affective and anxiety disorders. For example, metabolic imaging studies have helped identify cortical and subcortical areas of the brain associated with psychiatric pathologies. Similarly, anatomical tracing work in non-human primates have provided insight into the organization of networks involved with these areas. More recently, diffusion-tensor imaging (DTI) tractography has shown that CSTC projections from the ventral anterior internal capsule/ventral striatum (VC/VS) and sub-callosal cingulate white matter, which are the two most actively researched surgical target sites for psychiatric DBS, overlap in multiple regions of the brain associated with anti-depressant responses. Anatomical tracing work and DTI tractography studies suggest that while the general trajectory of axonal pathways can overlap, anatomical functional segregation is typically maintained (Gutman, D. A. et al., "A tractography analysis of two deep brain stimulation white matter targets for depression," Biol. Psychiatry 65 (4), 276-282 (2009) (hereinafter "Gutman et al., 2009"), the entire contents of which is hereby incorporated by reference herein). However, these imaging and anatomical techniques only provide pieces of the complete picture. As such, methodological refinements are required before these techniques can be used to fully describe the neural networks typically associated with psychiatric disease and other disorders and clinical outcomes.

Abnormal activity in the amygdala, thalamus, and orbitofrontal and anterior cingulate cortices has prompted different surgical target sites to be attempted. DBS of the ventral anterior internal capsule/ventral striatum (VC/VS) has already generated long-term improvement in both TRD and OCD patients (Malone, Jr., D. A. et al., "Deep brain stimulation of the ventral capsule/ventral striatum for treatment-resistant depression," Biol. Psychiatry 65 (4), 267-275 (2009) (hereinafter "Malone, Jr. et al., 2009"), the entire contents of which is hereby incorporated by reference herein). Similarly, DBS of subgenual cingulate white matter has produced sustained improvement in depressive symptoms of TRD patients (Lozano et al., 2008). However, questions still remain on which anatomical target sites or regions and axonal pathways are explicitly responsible for the therapeutic benefits of DBS for psychiatric and other disorders.

SUMMARY

The present invention relates to modulation of neuronal activity to affect psychiatric; pain; and other neurological activities, functions, disorders and conditions of a patient. In a preferred embodiment, the patient is a mammalian patient and in a more preferred embodiment, the patient is a human.

According to an example embodiment of the present invention, a method for generating a target stimulation region includes: for a plurality of electrode stimulations, identifying, by a computer processor, which neural elements were indicated to have been activated in a predetermined threshold number of the plurality of electrode stimulations; and outputting, by the processor, the identified neural elements as a target stimulation region for producing a clinical effect.

According to an example embodiment of the present invention, a method for generating a target stimulation region includes: for a plurality of electrode stimulations associated with a clinical effect, identifying, by a computer processor, which axons were indicated to have been activated in a predetermined threshold number of the plurality of electrode stimulations; and outputting, by the processor, the identified axons as a target stimulation region for producing the clinical effect.

According to an example embodiment of the present invention, a method for identifying a target stimulation region associated with a clinical outcome, for treatment of a disorder includes obtaining imaging data representing a region of a patient's brain, the imaging data including an indication of an electrode location of an electrode that has been guided into the region of the brain; using diffusion tractography on the imaging data to generate an axonal or neural element model of the patient; activating the electrode to deliver an electrical signal to the modeled axons or neural elements; and identifying the target stimulation region as a combination of at least a subset of those of the modeled axons or neural elements identified as activated by the delivery of the electrical signal.

According to a further example embodiment of the present invention, a computer-implemented method of providing a therapeutic stimulation of an anatomical region of a patient includes: selecting, by a computer processor, a stored target stimulation region; and outputting and/or applying stimulation settings for producing a region of estimated activation based on the selected target stimulation region, where the selected target stimulation region is formed of a collection of identified axons or other neural elements.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The drawings illustrate generally, by way of example, but not by way of limitation, various embodiments discussed in the present document.

FIG. 6 shows patient classification and grouping according to clinical outcomes, according to an example embodiment of the present invention.

DETAILED DESCRIPTION

Figure 1:
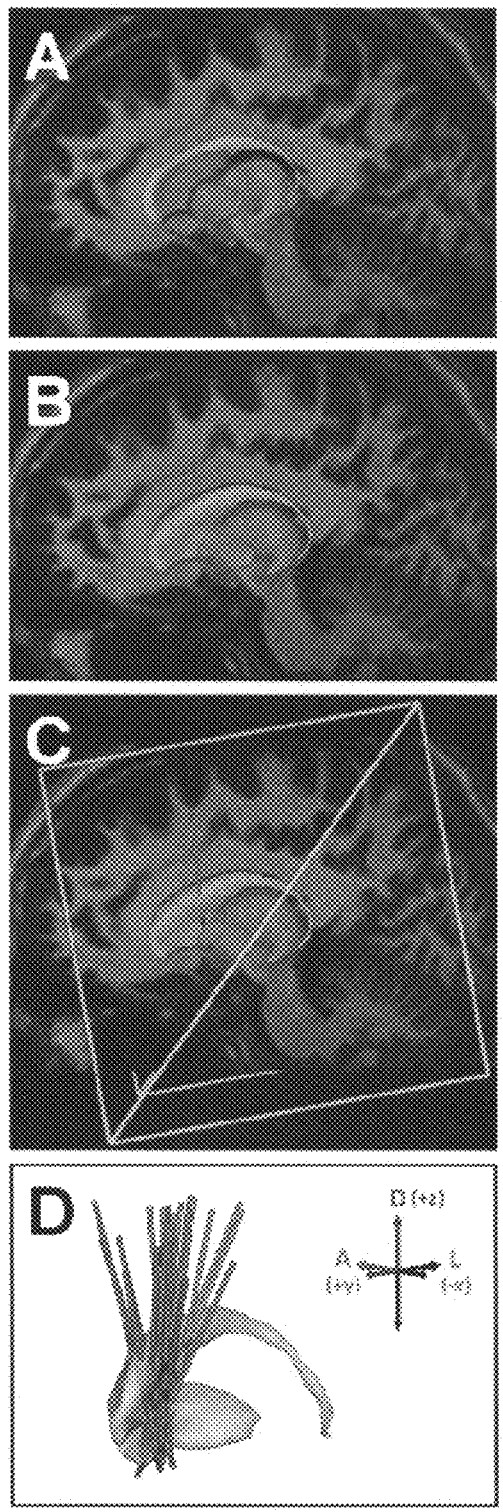
FIG. 1 shows anatomical models pertaining to DBS, according to an example embodiment of the present invention. Part A of FIG. 1 shows 3D surfaces representing various nuclei displayed on a sagittal view of a patient Magnetic Resonance Image (MRI). Part B of FIG. 1 shows nuclei surfaces translated, rotated, and scaled to improve the fit of the visible anatomy on the patient's MRI. Part C of FIG. 1 shows a virtual DBS electrode incorporated into the model by using the patient-specific stereotactic intra-operative electrode location. Part D of FIG. 1 shows all virtual DBS electrodes mapped onto a common anatomical framework defined within the diffusion tensor atlas brain.

The following detailed description includes references to the accompanying drawings, which form a part of the detailed description. The drawings show, by way of illustration, specific example embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

The present invention relates to modulation of neuronal activity to affect psychiatric; pain; and other neurological activities, functions, disorders and conditions. Non-limiting examples of psychiatric disorders include TRD and OCD, addiction, bipolar disorder, schizophrenia, panic and anxiety disorders, and post-traumatic stress disorders. The modulation can be accomplished, for example, by chemical, biological, electrical or ablational means.

More specifically, the present invention is directed to methods for treating psychiatric disorders; pain; and other neurological activities, functions, disorders and conditions by identifying and substantially activating target stimulation regions (also referred to herein as target anatomical regions of stimulation) to achieve therapeutic benefits. An example embodiment of the invention is described, which is directed to the treatment of treatment-resistant depression (TRD) and obsessive-compulsive disorder (OCD). However, the invention is not limited to these disorders and may include any neurological or psychiatric disorder.

According to an example embodiment of the present invention, a method for generating a target stimulation region includes: for a plurality of electrode stimulations, identifying, by a computer processor, which neural elements were indicated to have been activated in a predetermined threshold number of the plurality of electrode stimulations; and outputting, by the processor, the identified neural elements as a target stimulation region for producing a clinical effect.

In an example embodiment, all of the plurality of electrode stimulations are associated with the clinical effect, and the processor identifies the target stimulation region as probabilistically producing the clinical effect based on the association of the plurality of electrode stimulations with the clinical effect. A large number of stimulations may each be associated with a respective one or more clinical effects. Various groups of the stimulations may accordingly be formed, each group associated with a particular one of the clinical effects. A single stimulation associated with more than one of the defined clinical effects may be part of a number of groups. For each such group, the processor may identify the neural elements indicated to have been activated in the predetermined threshold number of the stimulations of the group, and set the respective collection of neural elements as a respective target stimulation region for the clinical effect with which the group is associated.

In an example embodiment, the neural elements are axons. In another example embodiment, the neural elements are dendrites. In another example embodiment, the neural elements are the cell bodies. Although reference is made below to axons, it is understood that applications of the methods of the present invention apply to other components of a neuron such as the cell body and dendrites.

In an example embodiment, the electrode stimulations are performed on at least one patient, and the method further includes: generating for each of the at least one patient a respective axonal model; and, for each of the electrode stimulations, generating a respective stimulation model of those axons of the axonal model, of the patient on which the stimulation was performed, which were activated by the respective electrode stimulation. Further, the identifying is based on the generated stimulation models.

In an example embodiment, the at least one axonal model is generated using diffusion tensor tractography.

In an example embodiment, the method further includes obtaining, for each of the at least one patient, respective imaging data of an anatomical region of the respective patient, and the axonal model generated for the respective patient is generated based on the respective imaging data of the patient. In an example embodiment, the anatomical region is the brain.

In an example embodiment, the at least one patient includes a plurality of patients.

In an example embodiment, each of the electrode stimulations is performed using one or more electrode leadwires that each includes one or more electrodes.

In an example embodiment, the threshold is 75%.

For example, an electrode leadwire may be implanted in each of a plurality of patients. One or more medical images, e.g., of one or more imaging modalities, such as MRI or computed tomography (CT), may be generated of a relevant anatomical region, e.g., the brain, of each of the patients in which the leadwire was implanted. A processor may apply diffusion tensor tractography to the medical images to generate an axonal model of the relevant anatomical region for each of the patients. One or more stimulations may be applied to each of the patients via the implanted electrode leadwire.

For each of the stimulations, the processor may generate a respective model of the tissue activated by the stimulation. For example, actual electric parameters may be measured for the stimulations. Alternatively, for each stimulation, the electric fields may be modeled based on (a) the patient's respective axonal model, (b) the stimulation parameters of the respective stimulation, and (c) the location of the electrode leadwire relative to the patient anatomy. The model of the tissue activated may be generated by applying the electric field model to the generated axonal model.

The patients may be grouped based on therapeutic effect. For example, clinicians, patients, and/or sensors may provide the system information concerning the therapeutic effect, if any, of the applied stimulation.

For each patient group, the system may compare the axons activated by their respective stimulations as indicated by the models of tissue activated to find which axons were activated in a threshold number, e.g., 75%, of the stimulations of the patients of the group. The processor may select all such axons as a new target stimulation region for producing the therapeutic effect with which the patients of the group are associated.

It is noted that more than one stimulation can be performed on a single patient, for example, using different parameter settings. Different axon activation models may be generated for different stimulations of the same patient. Moreover, the patient may be grouped into different groups for different ones of the stimulations.

In an example embodiment, a stimulation may be associated with a plurality of stimulation effects, and may accordingly be grouped in a number of groups.

According to an example embodiment of the present invention, a non-transitive, hardware, computer-readable medium has stored thereon instructions executable by a processor, the instructions which, when executed by the processor, cause the processor to perform a method for generating a target stimulation region, the method including: for a plurality of electrode stimulations associated with a same clinical effect, identifying which axons were activated in a predetermined threshold number of the plurality of electrode stimulations; and outputting the identified axons as a target stimulation region for producing the clinical effect.

According to an example embodiment of the present invention, a system for generating a target stimulation region includes a computer processor configured to: for a plurality of electrode stimulations associated with a same clinical effect, identify which axons were activated in a predetermined threshold number of the plurality of electrode stimulations; and output the identified axons as a target stimulation region for producing the clinical effect.

According to an example embodiment of the present invention, a computer-implemented method of providing a therapeutic stimulation of an anatomical region of a patient includes: selecting, by a computer processor, a stored target stimulation region; and outputting and/or applying stimulation settings for producing a region of estimated activation based on the selected target stimulation region, where the selected target stimulation region is formed of a collection of identified axons.

In an example embodiment, the collection of identified axons are axons identified to have been previously activated in a predetermined threshold number of stimulations associated with a desired therapeutic effect.

According to an example embodiment of the present invention, a method for identifying a target stimulation region associated with a clinical outcome, for treatment of a disorder includes obtaining imaging data representing a region of a brain of a patient, the imaging data including an indication of an electrode location of an electrode that has been guided into the region of the brain; using diffusion tractography on the imaging data to generate an axonal model of the patient; activating the electrode to deliver an electrical signal to the modeled axons; and identifying the target stimulation region as a combination of at least a subset of those of the modeled axons identified as activated by the delivery of the electrical signal.

In an example embodiment of the method, the disorder is a neurological or psychiatric disorder.

In an example embodiment of the method, the clinical outcome is therapeutic. In another embodiment, the clinical output is non-therapeutic.

In an example embodiment of the method, the therapeutic clinical outcome includes at least one of preventing, treating, and ameliorating one or more symptoms associated with the disorder.

In an example embodiment of the method, the imaging data is obtained from one of a magnetic resonance image (MRI) and a computed tomography (CT) image.

In an example embodiment of the method, the imaging data includes three-dimensional surface models of striatal, pallidal, and thalamic nuclei.

In an example embodiment of the method, the electrode is part of a deep brain stimulation (DBS) device.

In an example embodiment of the method, the diffusion tractography is performed on a region of interest that includes the electrode location.

In an example embodiment of the method, a computer simulation of induced action potentials on the modeled axons is used for the identification of activation of axons by the delivery of the electrical signal.

In an example embodiment, the method further includes selecting, based on the identified target stimulation region, a surgical site for implantation of an electrode.

In an example embodiment, the method further includes selecting, based on the identified target stimulation region, stimulation parameters to apply to one or more electrodes.

In an example embodiment of the method, the target stimulation region is identified by using a finite element model for modeling voltage distribution data representing inhomogeneous and anisotropic brain tissue, and at least one multi-compartment axon model for simulating axonal pathway trajectories.

The target stimulation region can include, but is not limited to, the ventral anterior internal capsule and ventral striatum (VC/VS) and axonal pathways lateral and medial to the ventral striatum or dorsal and lateral to the nucleus accumbens. The axonal pathways include, but are not limited to, those which pass through the ventral anterior internal capsule and course lateral and medial to the ventral striatum or dorsal and lateral to the nucleus accumbens.

In an example embodiment of the method, the target stimulation region is located within the ventral anterior internal capsule and ventral striatum in the brain.

In an example embodiment of the method, the target stimulation region includes at least one axonal pathway that traverses lateral and medial to the ventral striatum or dorsal and lateral to the nucleus accumbens in the brain.

Accordingly, the present invention includes methods that identify specific DBS-activated axonal pathways associated with, or responsible for, therapeutic improvements.

Example axonal pathways, particularly in TRD and OCD patients, include, but are not limited to nine specific axonal pathways.

In particular, one pathway courses along the ventro-medial surface of the dorsal striatum, from the dorso-lateral and posterior region of a region of interest (ROI) near an implanted DBS electrode, and then continues with antero-lateral projections relative to the boundaries of the ROI.

A second pathway courses along the ventro-medial surface of the dorsal striatum, from the dorso-lateral and posterior region of the ROI near an implanted DBS electrode, and then continues with ventro-latero-posterior projections relative to the boundaries of the ROI.

A third pathway courses along the ventro-medial surface of the dorsal striatum, from the dorso-lateral and posterior region of the ROI near an implanted DBS electrode, and then continues with ventro-medial anterior projections relative to the boundaries of the ROI.

A fourth pathway courses along the ventro-medial surface of the dorsal striatum, from the dorso-lateral and posterior region of the ROI near an implanted DBS electrode, and then continues with ventro-medial-posterior projections relative to the boundaries of the ROI.

A fifth pathway overlaps with the ventro-latero-posterior segment of the second pathway in its course along the ventro-medial portion of the posterior accumbens. This pathway passes dorsally along the lateral head of the caudate, continuing in a lateral and anterior direction over the central caudate.

A sixth pathway courses in an antero-posterior direction along the lateral head of the caudate nucleus, continuing ventrally along the posterior nucleus accumbens, then courses medial and ventral, and finally projects in an anterior direction.

A seventh pathway courses in an antero-posterior direction along the lateral head of the caudate nucleus, continuing ventrally along the posterior nucleus accumbens, and then continues medially along the posterior nucleus accumbens in a ventral direction within the ROI.

The sixth and seventh pathways overlap at their dorsal ROI boundaries and anterior segments before reaching the posterior nucleus accumbens.

The seventh pathway follows a more dorsal trajectory, continuing medially along the posterior nucleus accumbens in a ventral direction and overlapping with the seventh pathway.

The eighth pathway also follows a more dorsal trajectory, continuing medially along the posterior nucleus accumbens in a ventral direction and overlaps with the sixth pathway.

The ninth pathway courses along the ventromedial surface of the dorsal striatum, circling laterally around the central aspect of the lateral head of the caudate before continuing in an anterior direction.

Thus, the present invention utilizes the selective activation of target axonal pathways within CSTC networks for specific therapeutic effects observed in DBS patients.

In an example embodiment of the method, the target stimulation region is selected such that it does not overlap any axonal pathways that would produce a non-therapeutic effect if activated.

In an example embodiment of the method, the imaging data is obtained from more than one patient.

In an example embodiment of the method, the imaging data obtained from the more than one patient is mapped onto a brain atlas.

In an example embodiment of the method, the brain atlas is a diffusion-tensor brain atlas.

In an example embodiment of the method, the diffusion tractography techniques are performed on the diffusion-tensor brain atlas.

Accordingly, the present invention utilizes the combination of clinical data, diffusion tensor tractography, and computer models of patient-specific neurostimulation to identify particular axonal pathways activated by DBS and to determine their correlations with specific clinical outcomes.

The present invention thereby provides for identifying relationships between patient-specific DBS electrode location, model predictions of axonal activation, and clinical outcomes, to thereby improve clinical outcomes.

In example embodiments of the present invention, the DBS therapy involves bilateral VC/VS DBS therapy.

In an example embodiment the present invention, a DBS electrode is positioned near an axonal pathway of the brain, and an activation signal is applied to the axonal pathway for therapeutic improvement.

Accordingly, the method may be used to improve stimulation settings for DBS devices.

Example embodiments of the present invention provide methods of evaluating treatment resistant depression (TRD) and obsessive compulsive disorder (OCD) patients treated with DBS at a predetermined target stimulation region.

Described below is a study demonstrating that methods of the present invention are effective for preventing, treating, or ameliorating one or more symptoms associated with a neurological or psychiatric disorder. The study presents an example of how the combination of medical imaging, clinical outcome measures, and medical device technology can be used to gain a better understanding of the effects of a focal neurological or psychiatric treatment.

Seven TRD and five OCD patients received bilateral ventral anterior internal capsule/ventral striatum (VC/VS) deep brain stimulation (DBS) therapy. The term "bilateral" means that DBS is applied to both hemispheres of the brain. All patients underwent pre- and postoperative psychiatric evaluations. TRD patients were evaluated using the Hamilton Depression Rating Scale (HDRS), the Montgomery-Åsberg Depression Rating Scale (MADRS), and Global Assessment of Functioning (TRD GAF). OCD patients were evaluated with the Yale-Brown Obsessive Compulsive Scale (YBOCS) and Global Assessment of Functioning (OCD GAF).

After the patients were evaluated, axons of, and near, the VC/VS were activated. Individual axons activated by DBS in the seven TRD and five OCD patients were examined, and multiple pathways probabilistically-related to therapeutic and non-therapeutic clinical outcomes were identified. The results suggested that specific pathways lateral and posterior to the middle portion (on a dorsal-ventral direction) of the ventral striatum and pathways coursing dorsal and lateral to the ventral striatum are probabilistically-related either to therapeutic or non-therapeutic clinical outcomes.

One important aspect of the present invention is the recognition that the best therapeutic outcomes are achieved when axonal pathways associated only with responder groups were activated (each patient was classified either as in remission, a responder, or a non-responder). This is important because TRD and OCD are associated with distinct neural networks that include regions of overlap.

Furthermore, clinical outcomes deteriorated when therapeutic pathways overlapping with non-responder pathways were activated. Thus, therapeutic improvements require unique and selective activation of axonal pathways associated with indication-specific benefits, and the simultaneous activation of optimal and non-optimal pathways may deteriorate, slow down the progression of and even prevent clinical improvements. Specific details of the study are described below.

Patient Population

Axonal activation was analyzed in seven TRD and five OCD patients implanted bilaterally with quadripolar 3391 (formerly 3387-IES) DBS electrodes (1.27 mm diameter, 3 mm contact length, and 4 mm spacing between adjacent contacts, Medtronic, Minneapolis, Minn.). The patients were implanted and clinically monitored. Pertinent clinical data on the patients are summarized in Table 1.

TABLE 1

Patient information.

| Patient | Gender | Indication | Age at implant (years) | Last follow-up (months after implant) |
|---|---|---|---|---|
| CC1 | F | TRD | 37 | 41 |
| CC2 | F | TRD | 50 | 35 |
| CC3 | F | TRD | 27 | 30 |
| CC4 | F | TRD | 53 | 28 |
| CC5 | M | TRD | 54 | 19 |
| CC6 | F | TRD | 53 | 17 |
| CC7 | M | TRD | 23 | 15 |
| CC8 | M | OCD | 22 | 40 |
| CC9 | F | OCD | 35 | 77 |
| CC10 | M | OCD | 44 | 53 |
| CC11 | F | OCD | 60 | 9 |
| CC12 | M | OCD | 23 | 63 |

Anatomical Models of Patient-Specific VC/VS DBS

A computational DBS model, including anatomical and electrical components, for each of the brain hemispheres included in the study were created.

FIG. 1 shows anatomical models of DBS for patient CC5 on the left side of the brain. Part A shows 3D surfaces representing various nuclei (caudate nucleus—light blue, pallidum—dark blue, nucleus accumbens—pink, and thalamus—yellow) displayed on a sagittal view of the patient's magnetic resonance imaging (MRI). The nuclei surfaces were originally placed within the context of the patient's MRI based on the anterior and posterior commissure points (not visible).

Part B shows nuclei surfaces translated, rotated, and scaled (9 degrees of freedom) to improve the fit of the visible anatomy on the patient's MRI.

Part C shows a virtual 3391 DBS electrode incorporated into the model by using the patient-specific stereotactic intraoperative electrode location (defined using a Leksell stereotactic frame).

Part D is an oblique sagittal view showing all 24 virtual DBS electrodes (corresponding to the 24 brain hemispheres of the twelve patients included in the study) mapped onto a common anatomical framework defined within the diffusion tensor atlas brain, where active cathodes are shown in red, active anodes in blue, and inactive contacts in dark gray.

Each anatomical model included patient-specific imaging data, a virtual DBS electrode, and three-dimensional (3D) surface models of striatal, pallidal, and thalamic nuclei. The virtual electrode was created from a geometric representation of a 3391 DBS electrode. The 3D nuclei surfaces were extracted from a high-resolution MRI data set that was part of a diffusion-tensor (DT) atlas brain.

Each anatomical model was created by the following four steps:

First, fiducial markers were identified from a Leksell (Elekta, Stockholm, Sweden) stereotactic head frame visible in each pre-operative computed tomography (CT) data set, and co-registered with pre-existing fiducial models explicitly defined in stereotactic space. This allowed for the defining of the anterior (AC) and posterior (PC) commissures within a rigid coordinate system.

Second, each patient's specific pre-operative MRI and CT images were co-registered. All co-registrations were performed using a mutual information algorithm (Viola, I. et al., "Importance-driven focus of attention," IEEE Trans. Vis. Comput. Graph 12 (5), 933-940 (2006) (hereinafter "Viola et al., 2006").

Third, the 3D nuclei surfaces were co-registered with each patient-specific pre-operative MRI using Cicerone v1.2 (Miocinovic, S. et al., "stereotactic neurophysiological recording and deep brain stimulation electrode placement software system," Acta. Neurochir. Suppl. 97 (Pt 2), 561-567 (2007) (hereinafter "Miocinovic et al., 2007"). This was achieved by aligning the atlas brain with the stereotactic midline, and scaling it along its antero-posterior axis such that the AC and PC atlas coordinates matched the explicitly-defined MRI coordinates. Further alignment and scaling of the atlas surfaces were performed to fit visible nuclei on the MRI. Simple 4×4 affine transformation matrices were used to rotate, scale, and translate the atlas surfaces in 3D space (9 degrees of freedom) using Cicerone until a satisfactory co-registration was achieved (Lujan. J. L. et al., "Automated 3-dimensional brain atlas fitting to microelectrode recordings from deep brain stimulation surgeries," Stereotact. Funct. Neurosurg. 87 (4), 229-240 (2009)) (hereinafter "Lujan et al., 2009"). These brain nuclei surfaces served as a transition tool linking the anatomical patient space to the DT atlas brain, and allowed for performing transformations between the two corresponding coordinate systems.

Finally, as shown in Part C of FIG. 1, a virtual DBS electrode was seeded within each anatomical model using intra operative stereotactic coordinates. The correct placement of each virtual electrode was verified by co-registering pre- and post-operative CT scans. If the lead and contacts of the virtual DBS electrode were not properly centered within the hyperintense electrode artifact within the post-operative CT, Cicerone was used to manually translate the virtual DBS electrode in 3D space until it was properly aligned. This correction was necessary in only five hemispheres with an average displacement of 3.9 mm at the electrode tip.

Anatomical Framework for Identification of Axonal Pathways and Analysis of Axonal Activation A common anatomical framework on the left side of the DT atlas brain was defined and each virtual DBS electrode was mapped onto it from its patient-specific stereotactic space (FIG. 1, Part D). This mapping allowed for the identifying of axonal trajectories and the analyzing of axonal activation across patients. Individual electrode mappings were obtained by mathematically inverting the 4×4 affine transform matrices used to transform the atlas surfaces from DT atlas space into each patient-specific anatomical model.

Next, 3D trajectories of white matter axon fibers were identified that could be directly activated by DBS in these patients by using a streamline tractography algorithm (Wakana, S. et al., "Fiber tract-based atlas of human white matter anatomy," Radiology 230 (1), 77-87 (2004)) (hereinafter "Wakana et al., 2004"). Tractography was performed on a 60×60×60 mm region of interest (ROI) (see, FIG. 8, Part D below) encompassing all sites of therapeutic stimulation (i.e., active contacts for all 24 electrodes). This process inferred 228,960 different axon trajectories (9,540 trajectories for each electrode) originating from seed coordinate points within the DT atlas brain voxels. Seed points were distributed within 24 cylindrical regions, 52.5 mm long, and with 9.5 mm in radius (one for each virtual electrode). Each seed region was formed by nine planes oriented at 20 degree intervals and centered on the virtual DBS electrode. Within each plane, seeds were distributed at 1.9 and 0.5 mm horizontal and vertical resolutions, respectively. The trajectories resulting from these seeds propagated along the direction of the principal eigenvector of each voxel within the ROI, preserving voxel-to-voxel directional information. Fiber tracking from each seed continued until a highly isotropic region (fractional anisotropy<0.2) or the boundaries of the ROI were reached. Short axon trajectories with total lengths under 10.5 mm, or crossing into the electrode shaft, were discarded before the analysis.

Axon Models

A multi-compartment model of a myelinated axon was created to represent each of the 228,960 axon trajectories identified in the tractography analysis (McNeal, D. R. et al., "Analysis of a model for excitation of myelinated nerve," IEEE Trans. Biomed. Eng. 23 (4), 329-337 (1976)) (hereinafter "McNeal et al., 1976"). Axonal parameters for these models were defined according to previous published values for fiber diameters of 5.7 µm axons (McIntyre, C. C. et al., "Modeling the excitability of mammalian nerve fibers: influence of afterpotentials on the recovery cycle," J. Neurophysiol. 87 (2), 995-1006 (2002)) (hereinafter "McIntyre et al., 2002"). The geometry required to explicitly define the trajectory of each axon was determined using Matlab 7.6 (Mathworks Inc., Natick, Mass.).

Electrical Models of Patient-Specific VC/VS DBS

Figure 2:
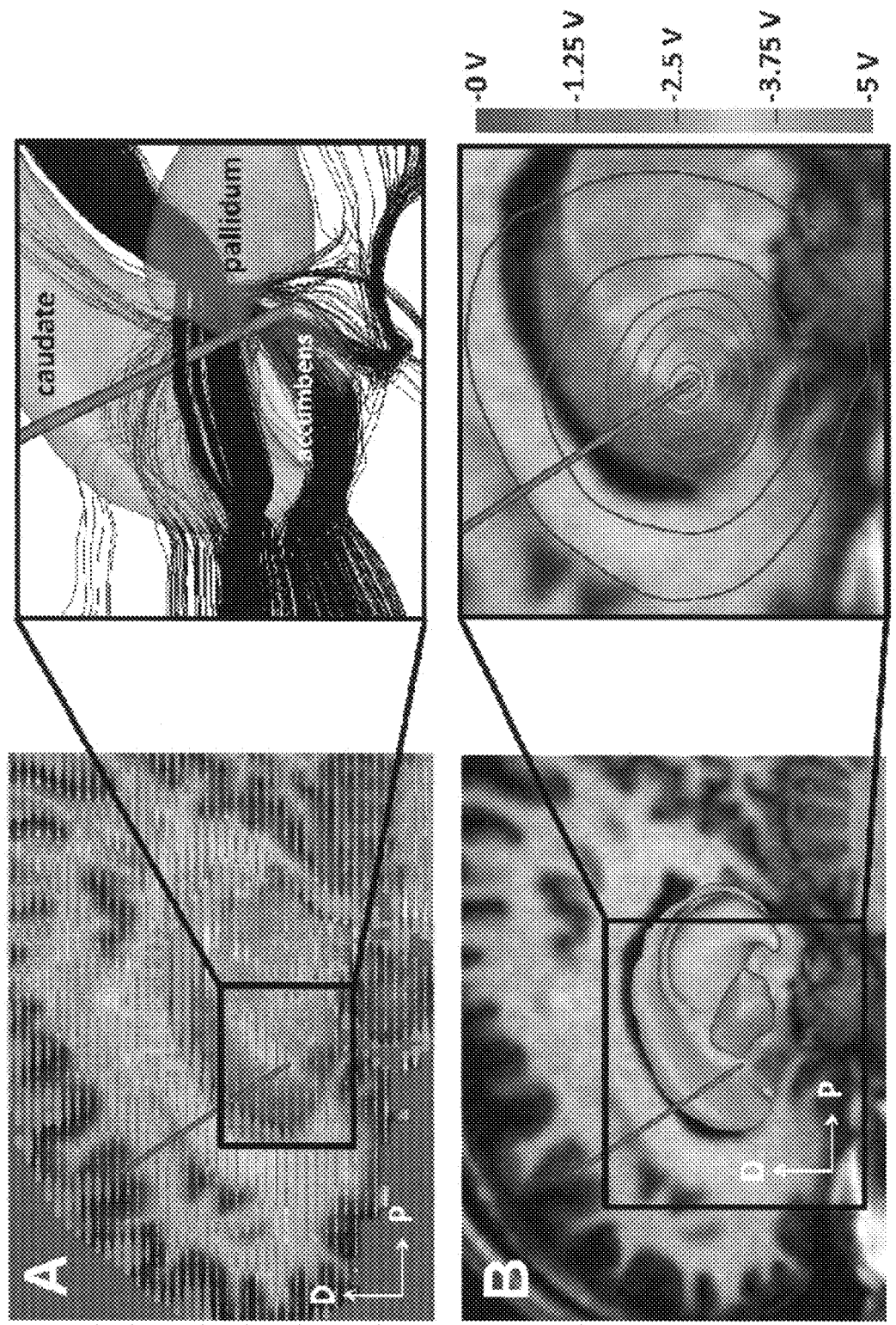
FIG. 2 shows electrical models of DBS, e.g., for identifying activated axons according to an example embodiment of the present invention. Part A of FIG. 2 shows the location of each patient-specific DBS electrode defined within the context of the diffusion-tensor atlas brain. Part B of FIG. 2 shows the diffusion-tensor atlas brain used to estimate conductivity-tensors used in a 3D finite element model of the DBS electric field.

FIG. 2 shows electrical models of DBS. Part A shows the location of each patient-specific DBS electrode defined within the context of the DT atlas brain. Each tensor (corresponding to one voxel) is represented by an ellipsoid, whose major axis indicates the preferred direction of water diffusivity. Fractional anisotropy is represented by the color of the ellipsoid (red—anisotropic, blue—isotropic). The inset shows the results of streamline tractography (black lines) performed from seed points defined around the patient-specific electrode location.

FIG. 2, Part B shows the DT atlas brain used to estimate conductivity-tensors used in a 3D finite element model of the DBS electric field. The inset shows voltage iso-contours generated by monopolar cathodic stimulation applied within the ventral anterior internal capsule.

Twenty-four electric field finite element models (FEM) were created that characterized each patient-specific voltage distribution within the brain (FIGS. 2B and 3A). Each FEM combined anisotropic properties of brain tissue, capacitance at the electrode-tissue interface, a thin layer of encapsulation around the electrode, and therapeutic stimulation settings (Chaturvedi, A. et al., "Patient-specific models of deep brain stimulation: Influence of field model complexity on neural activation predictions," Brain Stimulat. (2010)) (hereinafter "Chaturvedi et al., 2010").

Table 2 shows the stimulation settings used for each patient.

TABLE 2

Clinical stimulation settings. Electrode configuration indicates the contact number (0-3) followed by its type (cathodes are indicated by a negative sign and anodes by a positive sign). Only active contacts are shown in the electrode configuration.

| Patient | Frequency (Hz) | Pulsewidth (µs) | Amplitude (V) | Impedance (ohms) | Electrode configuration |
|---|---|---|---|---|---|
| | | | Left side | | |
| CC1 | 100 | 150 | 7 | 644 | 0+1− |
| CC2 | 130 | 150 | 8 | 1005 | 0−1−3+ |
| CC3 | 100 | 90 | 6.5 | 589 | 1−2−3+ |
| CC4 | 130 | 210 | 4 | 1359 | 0+3− |

TABLE 2-continued

Clinical stimulation settings. Electrode configuration indicates the
contact number (0-3) followed by its type (cathodes are indicated
by a negative sign and anodes by a positive sign).
Only active contacts are shown in the electrode configuration.

| Patient | Frequency (Hz) | Pulsewidth (µs) | Amplitude (V) | Impedance (ohms) | Electrode configuration |
|---|---|---|---|---|---|
| CC5 | 130 | 90 | 5 | 448 | 1-C+ |
| CC6 | 130 | 120 | 5.5 | 946 | 1-2-3+ |
| CC7 | 100 | 210 | 5 | 598 | 1-2-3+ |
| CC8 | 130 | 210 | 6 | 1452 | 1-C+ |
| CC9 | 100 | 180 | 8 | 1134 | 0-3+ |
| CC10 | 130 | 180 | 7 | 789 | 1-3+ |
| CC11 | 30 | 210 | 7 | 1060 | 0-C+ |
| CC12 | 100 | 120 | 6.5 | 714 | 1-C+ |
| Right side | | | | | |
| CC1 | 100 | 150 | 7 | 640 | 0+1- |
| CC2 | 130 | 150 | 7 | 751 | 0-1-3+ |
| CC3 | 100 | 150 | 8 | 557 | 1-2-3+ |
| CC4 | 130 | 210 | 5 | 1120 | 0-3+ |
| CC5 | 130 | 90 | 5 | 292 | 1-3-C+ |
| CC6 | 130 | 90 | 7 | 568 | 1-2-3+ |
| CC7 | 100 | 60 | 6 | 555 | 1-2-3+ |
| CC8 | 130 | 120 | 4 | 541 | 0-1- |
| CC9 | 100 | 180 | 8 | 1000 | 0-1-3+ |
| CC10 | 130 | 180 | 6 | 626 | 0-1-3+ |
| CC11 | 30 | 210 | 8 | 690 | 0-C+ |
| CC12 | 100 | 120 | 7 | 792 | 1-C+ |

The brain tissue was modeled as an inhomogeneous and anisotropic medium using the DT atlas brain (Miocinovic, S. et al., "Experimental and theoretical characterization of the voltage distribution generated by deep brain stimulation," Exp. Neurol. 216 (1), 166-176 (2009)) (hereinafter "Miocinovic et al., 2009"). The DBS electrode was modeled as a purely capacitive element with a 6.6 µF capacitance to reflect the large electrode contact size (Butson, C. R. et al., "Tissue and electrode capacitance reduce neural activation volumes during deep brain stimulation," Clin. Neurophysiol. 116 (10), 2490-2500 (2005)) (hereinafter "Butson et al., 2005"). A 0.5 mm-thick encapsulation layer surrounding the electrode was incorporated to account for charge transduction reactions and a 42% voltage drop at the electrode-tissue interface (Chaturvedi et al., 2010). Ohm's law was used to adjust the encapsulation layer conductivity (0.03 to 0.26 S/m) in each patient-specific model in order to match the measured clinical impedance (292 to 1452Ω). Patient-specific stimulation settings were applied to the electric field model and a Fourier FEM solver was used to solve Poisson's equation with Dirichlet and Neumann boundary conditions (Miocinovic et al., 2009). The solution provided the electric field within the brain tissue (FIG. 2, Part B inset and FIG. 3, Part A).

Axonal Activation

Figure 3:
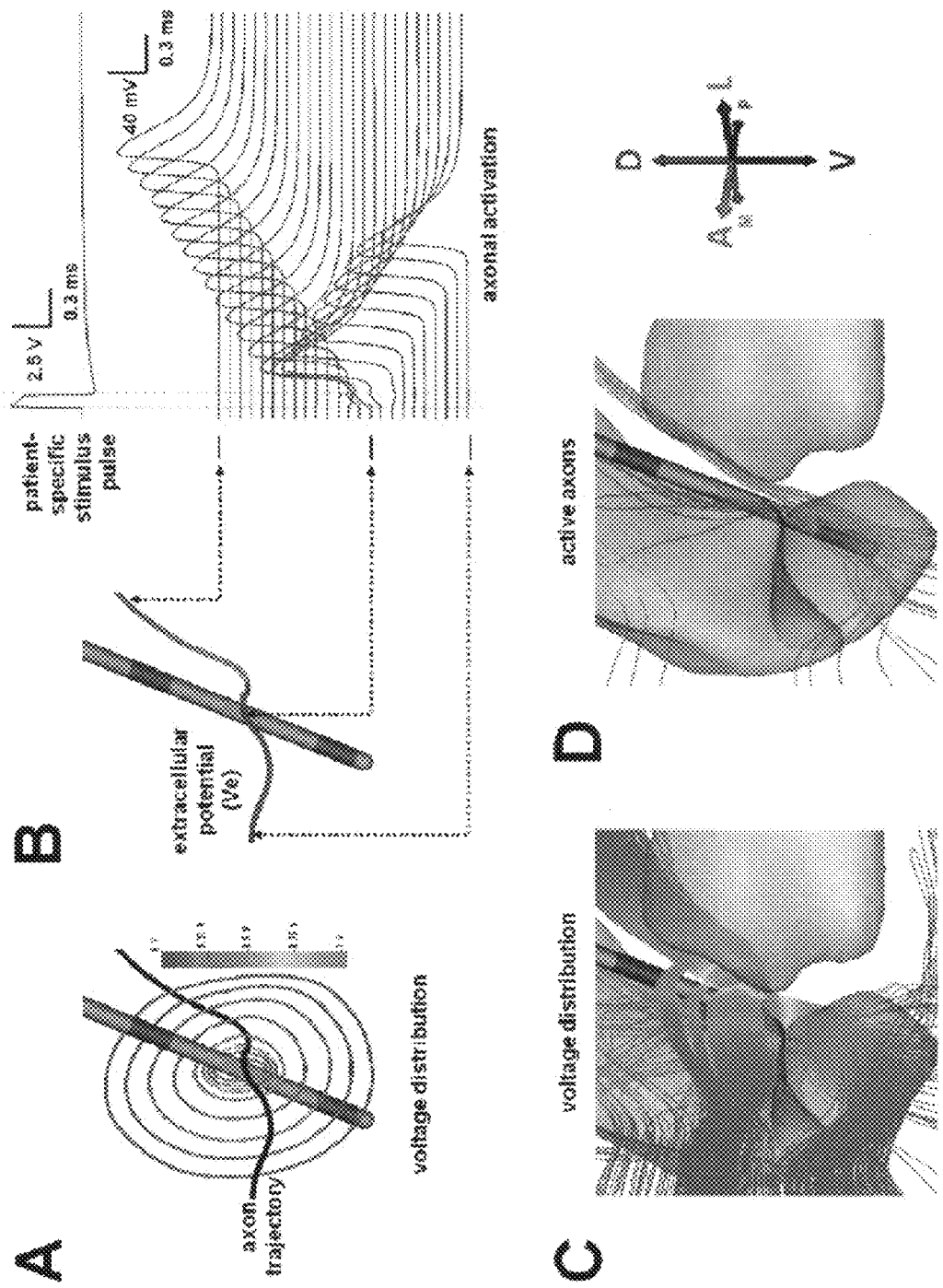
FIG. 3 shows a patient-specific model of axonal activation, according to an example embodiment of the present invention. Part A of FIG. 3 shows the electric field generated by patient-specific stimulation settings represented by iso-potential contours. Part B of FIG. 3 shows stimulation induced extracellular potentials interpolated onto an axon model. Part C of FIG. 3 shows extracellular voltages generated by patient-specific stimulation settings coupled to multi-compartment cable models of axons in the VC/VS. Part D of FIG. 3 shows axon models directly activated by DBS.

FIG. 3 shows a patient-specific model of axonal activation for patient CC5, for the left side of the brain. Part A shows the electric field generated by patient-specific stimulation settings represented by iso-potential contours.

Part B shows stimulation induced extracellular potentials (Ve) interpolated onto an axon model (red corresponds to the highest Ve magnitude and dark blue to the lowest). Action potentials initiate in the axon at the node of Ranvier where the second spatial derivative of the extracellular potential is largest (red trace). Once initiated, action potentials propagate in both directions along the axon (blue traces).

Part C shows extracellular voltages generated by patient-specific stimulation settings were coupled to multi-compartment cable models of axons in the VC/VS.

Part D shows axon models directly activated by DBS. The extracellular voltages were determined along each axon model by interpolating the patient-specific 3D electric fields onto each axon compartment.

Figure 4:
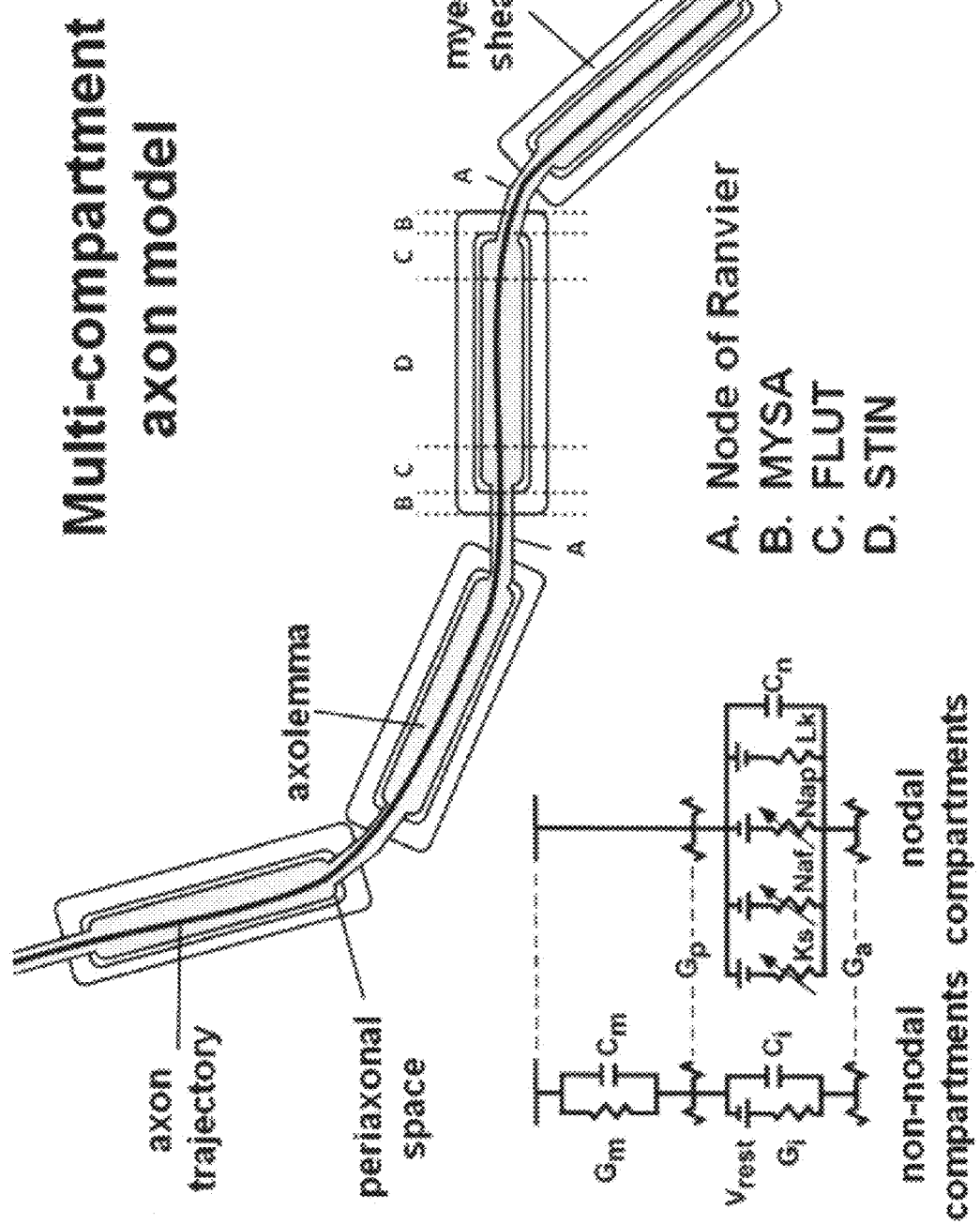
FIG. 4 shows a multi-compartment axon model, according to an example embodiment of the present invention.

FIG. 4 shows a multi-compartment axon model. Each axon trajectory defined by the streamline tractography was used to create a biophysical model capable of simulating action potential signaling. The model explicitly represented different subsections of the axon microstructure and myelin sheath. Hodgkin-Huxley type equations, customized for mammalian sodium and potassium channels, were used to simulate the transmembrane potential.

The axonal behavior was simulated in response to extracellular stimulation for all 228,960 axon models and 24 patient-specific DBS electric fields using NEURON 7.0 (Hines, M. L. et al., "The NEURON simulation environment," Neural computation 9 (6), 1179-1209 (1997)) (hereinafter "Hines et al., 1997"). Characterization of axonal activation, defined by the generation of a propagating action potential, required over 7 million computer simulations. These computer simulations were performed on a Linux-based high performance computing cluster with 15 individual computational nodes and a total of 68 cores running Rocks Clusters 5.3 (University of California at San Diego).

Correlation of Clinical Outcomes and Activation of Axonal Pathways

Following the approach of Malone et al. (Malone, Jr. et al., 2009) and Greenberg et al. (Greenberg, B. D. et al., "Deep brain stimulation of the ventral internal capsule/ventral striatum for obsessive-compulsive disorder: worldwide experience," Mol. Psychiatry 15 (1), 64-79 (2010)) (hereinafter "Greenberg et al., 2010"), TRD and OCD patients were classified into three sub-groups for each clinical outcome measure (x): remission (sub group x.1), nonremission but clinical response (sub-group x.2), and insufficient response or non responders (sub-group x. 3).

Remission for TRD patients was defined as a final score of 10 or less on the HDRS and MADRS measures (groups 1.1 and 2.1, respectively; see Table 3 below). For OCD patients, remission was defined as having a YBOCS score of 8 or less (group 5.1). No remission criteria were defined for TRD and OCD GAF measures (groups 3.1 and 4.1, respectively). Non-remission clinical response for HDRS (group 1.2) and MADRS (group 2.2) measures was defined as a minimum of 50% improvement from baseline. Clinical response for TRD and OCD GAF measures (groups 3.2 and 4.2, respectively) was defined as a follow-up score of at least 71. In contrast, clinical response for YBOCS was defined as at least 35% improvement (group 5.2). Patients unable to reach significance for therapeutic response were classified as non-responders (groups 1.3, 2.3, 3.3, 4.3 and 5.3 for HDRS, MADRS, TRD OAF, OCD OAF, and YBOCS, respectively).

Commonalities in axonal activation across patients were investigated to identify axonal pathways associated with therapeutic and non-therapeutic clinical outcomes. The patient-specific active axons were combined for each clinical group, and all axons within each group were analyzed to identify common activation across patients. The probability of producing the clinical outcome associated with each group (e.g., HDRS remission) by stimulating each axon was proportional to the number of patients for which the axon was activated by DBS within that group. Axons activated in 75% or more of patients within a group were considered associated with the corresponding clinical outcome. Common therapeutic active axons overlapping with common active axons identified in non-responder groups were excluded from the analysis. Individual axonal pathways were identified using an automated algorithm that grouped active axons with similar trajectories.

Identification of Individual Pathways

Figure 5:
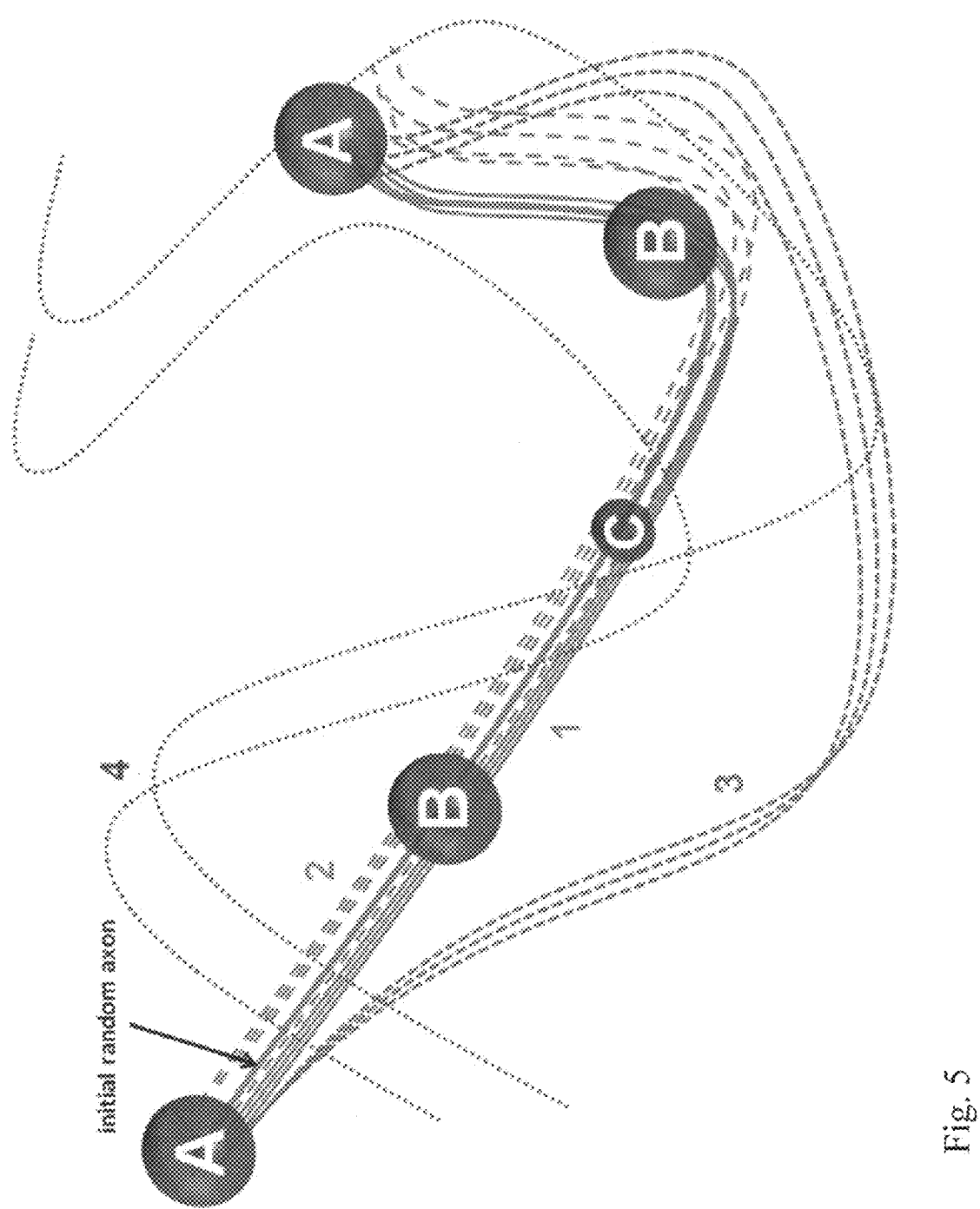
FIG. 5 shows identification of axonal pathways, according to an example embodiment of the present invention.

Distinct fiber pathways within groups of common activated axons were identified by using an automated algorithm that grouped individual axons with similar trajectories. Axons whose trajectories crossed five spheres centered at the boundaries (A), quarter lengths (B), and center (C) of a randomly-selected axon fiber as shown in FIG. 5, were grouped as part of the same pathway. In FIG. 5, each line style and color represents a distinct pathway. Pathways 1 and 2 share a similar trajectory but have one different boundary (pathway 2 crosses the first three spheres but not the last two). Conversely, pathways 1 and 3 share the same boundaries but differ in their intermediate trajectory (i.e., pathway 3 fails to cross the spheres at its quarter lengths and center). Pathway 4 has an entirely different trajectory (i.e., does cross any of the spheres for pathway 1).

The algorithm worked as follows:

First, all active axons within a clinical assessment group (e.g., HDRS remission, or group 1.1) were added to a list of trajectories to analyze.

Second, a single axon trajectory was randomly selected from the list, and spheres with 10 mm radius were centered at both boundaries (FIG. 5, A) and quarter-length sections of its trajectory (FIG. 5, B). A smaller fifth sphere with 5 mm radius was centered mid-length on the axon fiber (FIG. 5, C).

Third, the trajectories of the remaining axons in the list were examined, and those trajectories that intersected all five spheres centered on the initial fiber were grouped. The grouped axons were considered an individual pathway and were removed from the list.

Finally, a different axon was randomly selected from the list and the process repeated until all axons were assigned into a respective pathway.

Increasing the number of spheres or decreasing their radii decreased the tolerance for axonal trajectory grouping. The number and size of the spheres used in this study was selected after a trial-and-error process to achieve a balance between identification of distinct axonal pathways and pathway redundancy. Axon groups containing eight or less active axons were discarded to eliminate pathways with unusual trajectories and low probability of anatomical accuracy.

Statistical Analysis

Statistical analyses of clinical outcomes were performed using one-way analysis of variance (ANOVA) in Origin 7.5 (OriginLab Co., Northampton, Mass.). The significance level was set at $P<0.05$.

Results

Baseline and chronic DBS clinical outcome scores are summarized in Table 3.

TABLE 3

Clinical outcomes.

| | HDRS | | | | MADRS | | | |
|---|---|---|---|---|---|---|---|---|
| Patient | Baseline score | Last follow-up score | Score change (%) | Group | Baseline score | Last follow-up score | Score change (%) | Group |
| CC1 | 34 | 9 | 73.5 | 1.1 | 37 | 3 | 91.9 | 2.1 |
| CC2 | 27 | 27 | 0 | 1.3 | 28 | 18 | 35.7 | 2.3 |
| CC3 | 37 | 34 | 8.1 | 1.3 | 32 | 25 | 21.9 | 2.3 |
| CC4 | 32 | 1 | 96.9 | 1.1 | 25 | 0 | 100 | 2.1 |
| CC5 | 35 | 1 | 97.1 | 1.1 | 30 | 0 | 100 | 2.1 |
| CC6 | 26 | 2 | 92.3 | 1.1 | 26 | 0 | 100 | 2.1 |
| CC7 | 33 | 0 | 100 | 1.1 | 35 | 0 | 100 | 2.1 |
| CC8 | — | — | — | — | — | — | — | — |
| CC9 | — | — | — | — | — | — | — | — |
| CC10 | — | — | — | — | — | — | — | — |
| CC11 | — | — | — | — | — | — | — | — |
| CC12 | — | — | — | — | — | — | — | — |

| | GAF | | | | YBOCS | | | |
|---|---|---|---|---|---|---|---|---|
| Patient | Baseline score | Last follow-up score | Score change (%) | Group | Baseline score | Last follow-up score | Score change (%) | Group |
| CC1 | 45 | 60 | 25 | 3.3 | — | — | — | — |
| CC2 | 45 | 55 | 18.2 | 3.3 | — | — | — | — |
| CC3 | 50 | 51 | 2 | 3.3 | — | — | — | — |
| CC4 | 45 | 95 | 52.6 | 3.2 | — | — | — | — |
| CC5 | 45 | 71 | 36.6 | 3.2 | — | — | — | — |
| CC6 | 45 | 95 | 52.6 | 3.2 | — | — | — | — |
| CC7 | 41 | 95 | 56.8 | 3.2 | — | — | — | — |
| CC8 | 40 | 65 | 38.5 | 4.3 | 35 | 21 | 40 | 5.2 |
| CC9 | 30 | 60 | 50 | 4.3 | 36 | 21 | 41.7 | 5.2 |
| CC10 | 30 | 65 | 53.8 | 4.3 | 36 | 21 | 41.7 | 5.2 |
| CC11 | 30 | 45 | 33.3 | 4.3 | 77 | 28 | 63.6 | 5.2 |

TABLE 3-continued

| | | | Clinical outcomes. | | | | | |
|---|---|---|---|---|---|---|---|---|
| CC12 | 35 | 75 | 53.3 | 4.2 | 33 | 11 | 66.7 | 5.2 |

Baseline scores were measured the day before implantation.
Patient grouping is described in the form X, Y, where X refers to the corresponding outcome measure (1 = HDRS, 2 = MADRS, 3 = TRD GAF, 4 = OCD GAF, 5 = YBOCS) and Y refers to the type of clinical response (1 = remission, 2 = non-remission but clinical response, 3 = insufficient response or no response).

The mean HDRS, MADRS, and TRD GAF improvements from baseline were 66.8±43.7, 78.5±34.3 and 34.8±20.7 percent, respectively. One-way ANOVA of HDRS, MADRS, and TRD GAF scores showed sustained and significant improvement (p=0.002, p=0.0001, and p=0.002, respectively). Similarly, mean YBOCS and OCD GAF improvements were 50.7±13.2 and 45.8±9.3 percent, respectively. ANOVA also showed significant improvements from baseline in YBOCS and OCD GAF scores (p=0.03, and p=0.0005, respectively). Overall, the mean GAF outcome scores for all 12 patients increased from 40.1±7.1 to 69.3±17.5. According to individual HDRS scores, five TRD patients (CC1, CC4-CC7) were classified as in remission, and two patients (CC2 and CC3) were classified as non-responders. HDRS scores for patient CC2 returned to baseline after an undetected battery depletion of the patient's left-side implantable pulse generator (IPG). Patient CC3 presented initial improvements that were not maintained over time. None of the TRD patients fell into the middle category of clinical responders. Follow-up MADRS scores and percent improvements resulted in identical patient classification to HDRS. All five OCD patients (CC8-CC12) were classified in the YBOCS clinical responders group. Patient C11 showed a large improvement at last follow-up (63.6%), but maintained a high level of impairment (YBOCS score of 28). Four TRD (CC4-CC7) and one OCD (CC12) patients showed final clinical GAF scores of 71 or higher, thereby designating them as clinical responders for this measure. Patients CC4-CC7 achieved large improvements on both HDRS and MADRS measures (>92%), while patient CC12 achieved a large improvement on YBOCS (>66%).

As mentioned above, a patient-specific DBS computational model for each subject was created. Diffusion tensor tractography generated a population of 228,960 axons within the DBS simulation environment. Application of patient-specific DBS electrode locations and stimulation settings to these axons enabled prediction of stimulation induced action potential generation. All axons that were active for patients were grouped within each clinical outcome classification. The probability of evoking each clinical outcome (associated with the current clinical group) by activating a specific axon was proportional to the number of patients within the group for which said axon was active. This patient classification (i.e., grouping) allowed for the identification of pathways associated with specific clinical improvements common across patients.

FIG. 6 shows patient classification and grouping according to clinical outcomes. Patients were grouped according to the clinical outcome scores and percent improvement at their last available follow up visit (only HDRS outcomes for TRD patients are shown for illustration purposes). The groups were numbered using two digits: the first digit indicates the evaluation measure (e.g., HDRS=1, YBOCS=5, etc.) and the second digit indicates the clinical outcome type (e.g., remission=1, non-remission but clinical response=2, nonresponse=3). Activated axons for each patient are indicated with "X". In the example data, axons 1, 4, 6, and 228,960 (solid rectangles) were commonly active across at least 75% of the remission group; axons 3 and 5 (dashed rectangles) were commonly active across 75% of the no response group; and axon 2 (dotted rectangle) was removed from the analysis because it was simultaneously activated in both responders and non-responders.

Figure 7:
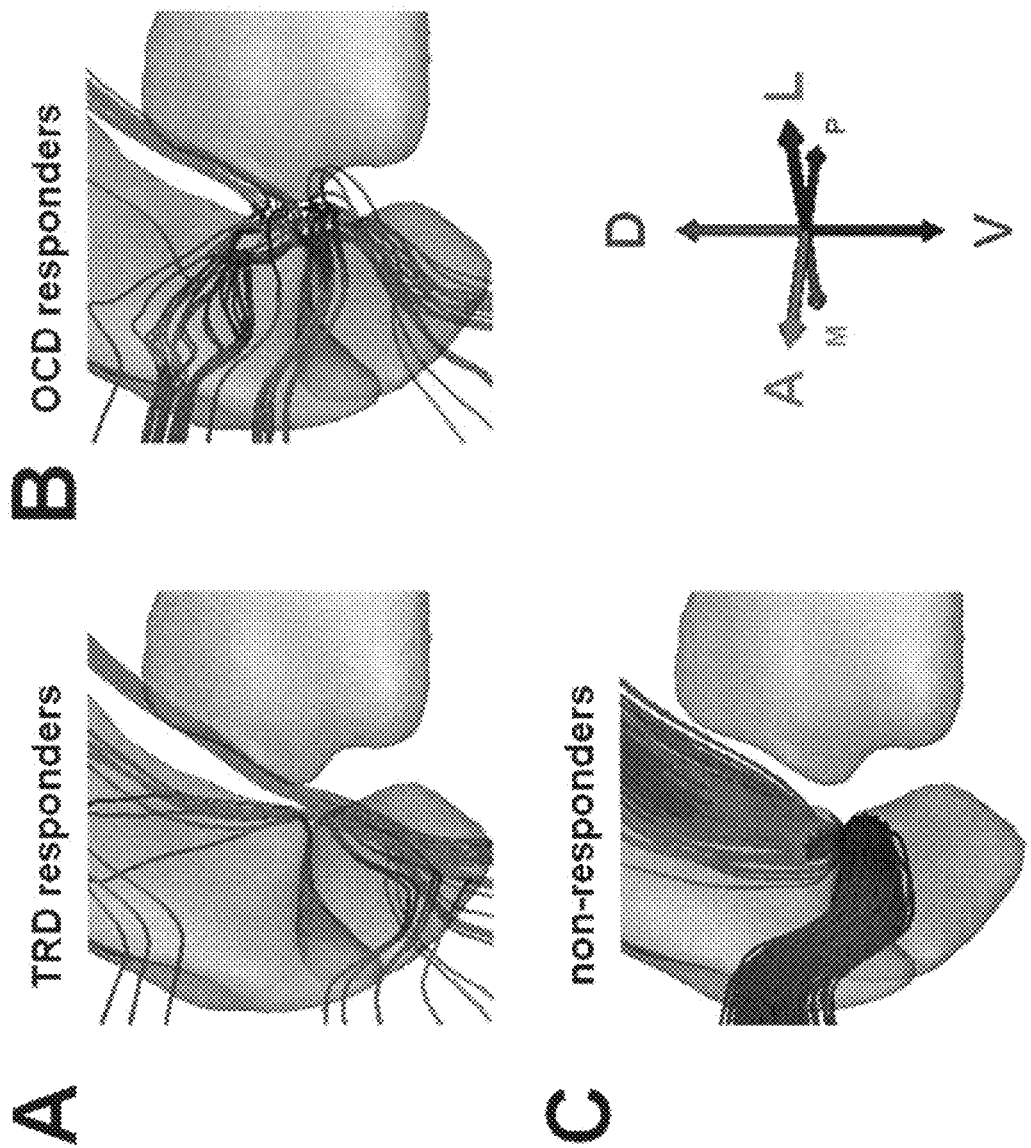
FIG. 7 shows therapeutic and non-therapeutic axonal activation, according to an example embodiment of the present invention. Part A of FIG. 7 shows activated axons common to at least 75% of the TRD responders. Part B of FIG. 7 shows activated axons common to at least 75% of the OCD responders. Part C of FIG. 7 shows activated axons common to at least 75% of the TRD and OCD patients who did not achieve clinical response.

Active axons within remission or responder groups that were also active in non-responders were excluded. FIG. 7 shows therapeutic and non-therapeutic axonal activation. This allowed to identify pathways associated exclusively with either therapeutic (FIG. 7, Part A and Part B) or non-therapeutic (FIG. 7, Part C) outcomes. FIG. 7, Part A shows activated axons common to at least 75% of the TRD responders. FIG. 7, Part B shows activated axons common to at least 75% of the OCD responders. FIG. 7, Part C shows activated axons common to at least 75% of the TRD and OCD patients who did not achieve clinical response (no OCD patients were classified as non-responders on the YBOCS but four OCD patients were classified as nonresponders according to their GAF outcome scores).

Figure 8:
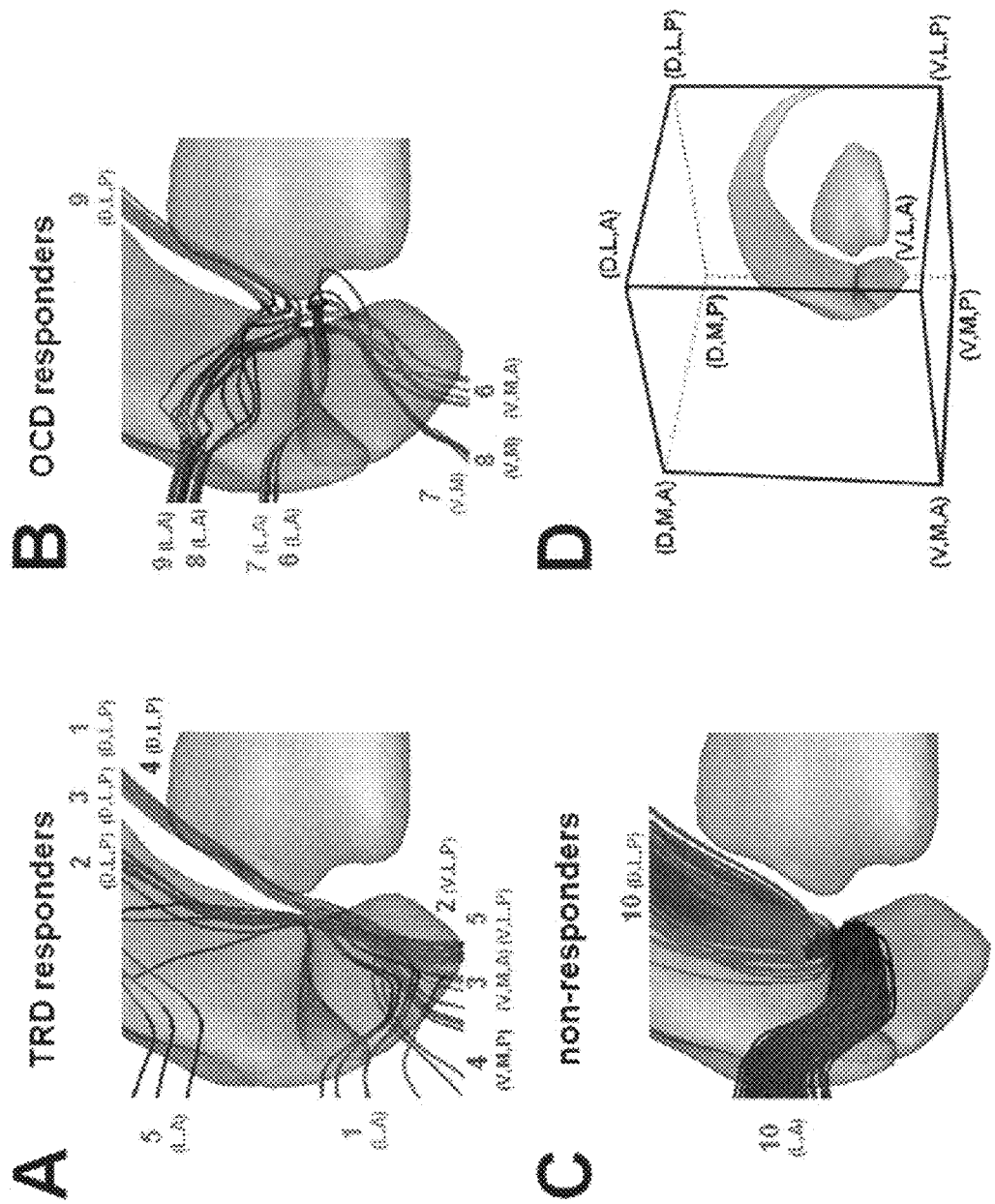
FIG. 8 shows outcome-specific axonal pathways, according to an example embodiment of the present invention. Part A of FIG. 8 shows common active pathways across 75% of the TRD responders. Part B of FIG. 8 shows common active pathways across OCD responders. Part C of FIG. 8 shows common active pathways across non-responders. Part D of FIG. 8 shows the ROI used to analyze the pathways identified by the streamline tractography.

FIG. 8, Part A shows common active pathways across 75% of the TRD responders. FIG. 8, Part B shows common active pathways across OCD responders. FIG. 8, Part C shows common active pathways across non-responders (no OCD patients were classified as non-responders on the YBOCS, but four OCD patients were classified as non-responders according to their GAF outcome scores). The ROI used to analyze the pathways identified by the streamline tractography is shown in FIG. 8, Part D. The numbers indicate distinct pathways identified using the algorithm described above, while the combinations of letters indicate the general location of the boundaries of each pathway with respect to the ROI (D=dorsal, V=ventral, A=anterior, P=posterior, M=medial, and L=lateral).

Nine distinct active pathways were identified (P1-9, the numbers correspond to pathway labels in FIG. 8) common to 75% or more of clinical responders. These pathways passed through the ventral anterior internal capsule (VAIC) and coursed lateral and medial to the ventral striatum, or dorsal and lateral to the nucleus accumbens. Despite this local overlap, their specific trajectories were different. It must be noted that the methodology employed in this study did not allow for the identification of the origin, termination, or direction of transmission of these axons with certainty. Instead, it provides a theoretical definition of the local axon trajectories activated by DBS within a region of interest (ROI) near the implanted DBS electrode (FIG. 8, Part D).

The first five distinct active pathways (P1-5) were common to 75% or more of TRD patients in the HDRS remission group (FIG. 8, Part A). Three of these pathways (P2-4) were also commonly activated across patients in the TRD GAF clinical response group. Pathways 1 through 4 coursed along the ventro-medial surface of the dorsal striatum, from the dorsolateral and posterior region of the ROI. These continued with antero-lateral (P1), ventro-latero-posterior (P2), ventro-medial anterior (P3), and ventro-medial-posterior (P4) projections relative to the boundaries of the ROI. The fifth pathway (P5) overlapped with the ventrolatero-posterior segment of pathway 2 in its course along the ventro-medial portion of the posterior nucleus accumbens. This pathway passed dorsally along the lateral head of the caudate, continuing in a lateral and anterior direction over the central caudate. The next four distinct active pathways (P6-9) were common to 75% or more of OCD responders (FIG. 8, Part B). Pathways 6 through 8 were common across the YBOCS clinical responders group. These pathways coursed in an antero-posterior direction along the lateral head of the caudate nucleus, continuing ventrally along the posterior accumbens. Pathways 6 and 7 overlapped at their dorsal ROI boundaries and anterior segments before reaching the posterior nucleus accumbens. Pathway 6 coursed medial and ventral after passing by the posterior nucleus accumbens, and finally projecting in an anterior direction. However, pathway 7 continued medially along the posterior nucleus accumbens in a ventral direction within the ROI. Pathway 8 followed a more dorsal trajectory, continuing medially along the posterior nucleus accumbens in a ventral direction and overlapping with pathway 7. Similarly, analysis of common activation for OCD GAF responders resulted in the identification of two active pathways. The first pathway overlapped with pathway 6, described previously. The second pathway (P9) coursed along the ventromedial surface of the dorsal striatum, circling laterally around the central aspect of the lateral head of the caudate before continuing in an anterior direction. Only one active pathway (P10) was common among 75% of patients who did not achieve clinical significance according to HDRS. TRD GAF, and OCD GAF (FIG. 8C). This pathway overlapped with the ventro-medial surface of the dorsal striatum and had a similar trajectory to therapeutic pathways in both patient populations (P1 and P9).

An example embodiment of the present invention is directed to one or more processors, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The one or more processors may be embodied in a server or user terminal or combination thereof. The user terminal may be embodied, for example, a desktop, laptop, hand-held device, Personal Digital Assistant (PDA), television set-top Internet appliance, mobile telephone, smart phone, etc., or as a combination of one or more thereof. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape. Such devices may be used for generating target stimulation regions, for obtaining from memory a previously stored target stimulation regions, and/or for selecting and/or applying stimulation parameters for an implanted electrode leadwire.

An example embodiment of the present invention is directed to one or more hardware computer-readable media, e.g., as described above, having stored thereon instructions executable by a processor to perform one or more of the methods described herein.

An example embodiment of the present invention is directed to a method, e.g., of a hardware component or machine, of transmitting instructions executable by a processor to perform one or more of the methods described herein.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and following claims.

What is claimed is:

1. A computer-implemented method for generating a target stimulation region, the method comprising:
   for a plurality of electrode stimulations performed on at least one patient, identifying, by a computer processor, which neural elements were indicated to have been activated in a predetermined threshold number of the plurality of electrode stimulations; and
   outputting, by the processor, the identified neural elements as a target stimulation region for producing a clinical effect;
   wherein:
      a respective axonal model is generated for each of the at least one patient;
      for each of the plurality of electrode stimulations performed on the at least one patient, a respective stimulation model is generated, the respective stimulation model being of those axons of the axonal model, of the patient on which the stimulation was performed, which were activated by the respective electrode stimulation; and
      the identifying is based on the stimulation models.

2. The method of claim 1, wherein the at least one axonal model is generated using diffusion tensor tractography.

3. The method of claim 1, further comprising:
   obtaining, for each of the at least one patient, respective imaging data of an anatomical region of the respective patient, wherein the axonal model generated for the respective patient is generated based on the respective imaging data of the patient.

4. The method of claim 3, wherein the anatomical region is the brain.

5. The method of claim 1, wherein the at least one patient includes a plurality of patients.

6. The method of claim 1, wherein each of the electrode stimulations is performed using one or more electrode lead-wires that each includes one or more electrodes.

7. The method of claim 1, wherein the threshold is 75%.

8. The method of claim 1, wherein all of the plurality of electrode stimulations are associated with the clinical effect, and the processor identifies the target stimulation region as probabilistically producing the clinical effect based on the association of the plurality of electrode stimulations with the clinical effect.

9. The method of claim 1, wherein the neural elements are axons.

10. A non-transitory computer-readable medium having stored thereon instructions executable by a processor, the instructions which, when executed by the processor, cause the processor to perform a method for generating a target stimulation region, the method comprising:
    for a plurality of electrode stimulations performed on at least one patient, identifying which neural elements were activated in a predetermined threshold number of the plurality of electrode stimulations; and
    outputting the identified neural elements as a target stimulation region for producing a clinical effect;

wherein:
a respective axonal model is generated for each of the at least one patient;
for each of the plurality of electrode stimulations performed on the at least one patient, a respective stimulation model is generated, the respective stimulation model being of those axons of the axonal model, of the patient on which the stimulation was performed, which were activated by the respective electrode stimulation; and
the identifying is based on the stimulation models.

11. A system for generating a target stimulation region, the system comprising:
a computer processor configured to:
for a plurality of electrode stimulations performed on at least one patient, identify which neural elements were activated in a predetermined threshold number of the plurality of electrode stimulations; and
output the identified neural elements as a target stimulation region for producing the clinical effect;
wherein the identification is based on a plurality of stimulation models that are each (a) generated for a respective one of the plurality of electrode stimulations and (b) of those axons, of a respective axonal model generated for a respective one of the at least one patient on which the respective stimulation was performed, which were activated by the respective electrode stimulation.

12. A computer-implemented method of providing a therapeutic stimulation of an anatomical region of a patient, the method comprising:
selecting, by a computer processor, a collection of complete neural elements from a stored model of neural elements and as a target stimulation region, the complete neural elements being identified individually on a neural element by neural element basis, such that, for each of the neural elements that are part of the target stimulation region, the entirety of the neural element is within the target stimulation region; and
at least one of outputting and applying stimulation settings for producing a region of estimated activation based on the selected target stimulation region;
wherein:
the neural elements are one of (a) nerve fibers and (a) a particular element of nerve fibers; and
the selection is based on the selected neural elements having been activated in a threshold number of prior stimulations.

13. The method of claim 12, wherein the selection is based on the threshold number of stimulations being associated with a desired therapeutic effect.

14. The method of claim 12, wherein the neural elements are axons.

15. A method for identifying a target stimulation region associated with a clinical outcome, for treatment of a disorder, the method comprising:
(a) obtaining imaging data representing a region of a brain of a patient, the imaging data including an indication of an electrode location of an electrode that has been guided into the region of the brain;
(b) using diffusion tractography on the imaging data to generate an neural model of the patient;
(c) during a session, activating the electrode to deliver an electrical signal to the modeled neural elements of the neural model;
(d) recording the clinical outcome in association with the activation; and
(e) identifying the target stimulation region as a combination of at least a subset of those of the modeled neural elements identified as activated a threshold number of times by electrical signal delivery during a plurality of sessions including the session of step (c).

16. The method of claim 15, wherein the disorder is a neurological or psychiatric disorder.

17. The method of claim 15, wherein the clinical outcome is therapeutic.

18. The method of claim 17, wherein the therapeutic clinical outcome includes at least one of preventing, treating, and ameliorating one or more symptoms associated with the disorder.

19. The method of claim 15, wherein the imaging data is obtained from one of a magnetic resonance image (MRI) and a computed tomography (CT) image.

20. The method of claim 15, wherein the imaging data includes three-dimensional surface models of striatal, pallidal, and thalamic nuclei.

21. The method of claim 15, wherein the electrode is part of a deep brain stimulation (DBS) device.

22. The method of claim 15, wherein the diffusion tractography is performed on a region of interest that includes an electron location.

23. The method of claim 15, wherein the neural model is an axonal model and the neural elements are axons.

24. The method of claim 23, wherein a computer simulation of induced action potentials on the modeled axons is used for the identification of activation of axons by the delivery of the electrical signal.

25. The method of claim 15, wherein the target stimulation region is identified by using a finite element model for modeling voltage distribution data representing inhomogeneous and anisotropic brain tissue, and at least one multi-compartment axon model for simulating axonal pathway trajectories.

26. The method of claim 15, wherein the target stimulation region is located within the ventral anterior internal capsule and ventral striatum in the brain.

27. The method of claim 15, wherein the target stimulation region includes at least one axonal pathway that traverses lateral and medial to the ventral striatum or dorsal and lateral to the nucleus accumbens in the brain.

28. The method of claim 27, wherein the target stimulation region is selected such that it does not overlap any axonal pathways that would produce a non-therapeutic effect if activated.

29. The method of claim 15, wherein the imaging data is obtained from more than one patient.

30. The method of claim 29, wherein the imaging data obtained from the more than one patient is mapped onto a brain atlas.

31. The method of claim 30, wherein the brain atlas is a diffusion-tensor brain atlas.

32. The method of claim 31, wherein the diffusion tractography techniques are performed on the diffusion-tensor brain atlas.

33. The method of claim 15, further comprising:
selecting, based on the identified target stimulation region, a surgical site for implantation of an electrode.

34. The method of claim 15, further comprising:
selecting, based on the identified target stimulation region, stimulation parameters to apply to one or more electrodes.

* * * * *